United States Patent
Dufour et al.

(10) Patent No.: US 11,547,388 B2
(45) Date of Patent: Jan. 10, 2023

(54) CORRECTING PROBE INDUCED DEFORMATION IN AN ULTRASOUND FUSING IMAGING SYSTEM

(71) Applicant: KONINKLIJKE PHILIPS N.V., Eindhoven (NL)

(72) Inventors: Cecile Dufour, Paris (FR); Roberto José Ardon, Sèvres (FR); Gary Cheng-How Ng, Redmond, WA (US); Thomas Shu Yin Tang, Ontario (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 343 days.

(21) Appl. No.: 16/301,895

(22) PCT Filed: May 22, 2017

(86) PCT No.: PCT/EP2017/062314
§ 371 (c)(1),
(2) Date: Nov. 15, 2018

(87) PCT Pub. No.: WO2017/202795
PCT Pub. Date: Nov. 30, 2017

(65) Prior Publication Data
US 2019/0290241 A1    Sep. 26, 2019

(30) Foreign Application Priority Data
May 23, 2016  (EP) ..................................... 16305588

(51) Int. Cl.
*A61B 8/00* (2006.01)
*A61B 90/00* (2016.01)
(Continued)

(52) U.S. Cl.
CPC ............ *A61B 8/4254* (2013.01); *A61B 8/469* (2013.01); *A61B 8/485* (2013.01); *A61B 8/5261* (2013.01);
(Continued)

(58) Field of Classification Search
CPC ..... A61B 8/4254; A61B 8/469; A61B 8/5261; A61B 2090/364; A61B 2034/2051;
(Continued)

(56) References Cited

U.S. PATENT DOCUMENTS 6,567,087 B1 * 5/2003 Reid ....................... G06T 17/20
                                              345/428
7,793,217 B1 * 9/2010 Kim ....................... G16H 80/00
                                              715/255
(Continued)

FOREIGN PATENT DOCUMENTS

JP    2010131269 A    6/2010
JP    2011083636 A    4/2011
(Continued)

OTHER PUBLICATIONS

International Search and Written Opinion for International Application No. PCT/EP2017/062314, dated Sep. 25, 2017, 15 pages.
(Continued)

*Primary Examiner* — Luther Behringer

(57) ABSTRACT

A fusion imaging system co-registers and fuses real time ultrasound images with reference images such as those produced by MRI or CT imaging. In an illustrated implementation, previously acquired CT or MRI or ultrasound images are loaded into the system. An ultrasound system is operated in conjunction with a tracking system so that the ultrasound probe and images can be spatially tracked. A computerized image processor registers the probe position with a reference image of the anatomy being scanned by the
(Continued)

probe and determines whether the probe appears to be inside the skin line of the subject. If that is the case it is due to probe compression of the subject, and the reference image is modified to locate the skin line in the reference image in front of the ultrasound probe. The modified reference images can then be readily co-registered and fused with the ultrasound images produced by the probe.

12 Claims, 4 Drawing Sheets

(51) Int. Cl.
    *A61B 8/08*           (2006.01)
    *G06T 7/00*         (2017.01)
    *A61B 34/20*        (2016.01)

(52) U.S. Cl.
    CPC ............ *A61B 90/36* (2016.02); *G06T 7/0014* (2013.01); *A61B 8/463* (2013.01); *A61B 8/58* (2013.01); *A61B 2034/2051* (2016.02); *A61B 2090/364* (2016.02); *A61B 2090/365* (2016.02); *A61B 2090/378* (2016.02); *G06T 7/0012* (2013.01)

(58) Field of Classification Search
    CPC ........ A61B 2090/365; A61B 2090/378; A61B 8/00; A61B 8/08; G06T 7/0014; G06T 7/0012; G06T 7/00
    See application file for complete search history.

(56) References Cited

U.S. PATENT DOCUMENTS

| | | | |
|---|---|---|---|
| 8,165,327 B2* | 4/2012 | Pape | ..................... H04R 25/505 |
| | | | 381/312 |
| 8,165,372 B2 | 4/2012 | Ishikawa et al. | |
| 9,471,981 B2 | 10/2016 | Arai et al. | |
| 2005/0119568 A1* | 6/2005 | Salcudean | ........... G01S 15/8977 |
| | | | 600/437 |
| 2007/0167784 A1 | 7/2007 | Shekhar et al. | |
| 2008/0186378 A1 | 8/2008 | Shen et al. | |
| 2011/0178389 A1 | 7/2011 | Kumar et al. | |
| 2012/0063655 A1* | 3/2012 | Dean | ....................... G06T 17/00 |
| | | | 382/128 |
| 2012/0123263 A1* | 5/2012 | Osaka | .................. A61B 5/0051 |
| | | | 600/438 |
| 2014/0193053 A1 | 7/2014 | Kadoury et al. | |
| 2014/0341449 A1* | 11/2014 | Tizhoosh | ............. A61B 8/5261 |
| | | | 382/128 |
| 2015/0209599 A1* | 7/2015 | Schlosser | ............. A61B 6/4417 |
| | | | 600/427 |
| 2016/0000519 A1* | 1/2016 | Dehghan Marvast | . A61B 34/20 |
| | | | 600/424 |
| 2016/0007970 A1 | 1/2016 | Dufour et al. | |
| 2016/0030008 A1 | 2/2016 | Gerard | |
| 2018/0296185 A1* | 10/2018 | Cox | ....................... A61B 8/483 |

FOREIGN PATENT DOCUMENTS

| | | | | |
|---|---|---|---|---|
| JP | 2012217769 A | * | 11/2012 | ........... A61B 8/5261 |
| JP | 2012217769 A | | 11/2012 | |
| WO | 2012141184 A1 | | 10/2012 | |
| WO | 2013141974 A1 | | 9/2013 | |
| WO | WO 2014/132209 | * | 9/2014 | ............... A61B 8/00 |

OTHER PUBLICATIONS

Kadoury, et al., "A Model-Based Registration Approach of Preoperative MRI With 3D Ultrasound of the Liver for Interventional Guidance Procedures", Biomedical Imaging, 2012 9th IEEE International Symposium On, IEEE, May 2, 2012, pp. 952-955.

* cited by examiner

CORRECTING PROBE INDUCED DEFORMATION IN AN ULTRASOUND FUSING IMAGING SYSTEM

This application is the U.S. National Phase application under 35 U.S.C. § 371 of International Application No. PCT/EP2017/062314, filed on May 22, 2017, which claims the benefit of European Application Serial No. 16305588.2, filed May 23, 2016. These applications are hereby incorporated by reference herein.

FIELD OF THE INVENTION

This invention relates to medical diagnostic ultrasonic imaging and, in particular, to ultrasound fusion imaging systems which correct for probe induced deformation.

BACKGROUND OF THE INVENTION

Various medical diagnostic imaging systems have different characteristics which play important roles in diagnostic imaging. Magnetic resonance imaging (MRI) systems and computed tomography (CT) systems are known for producing highly resolved images of tissue and organs inside the body, but do not lend themselves well to high frame rate real time imaging. Ultrasound imaging, on the other hand, produces images with less resolution but at a high frame rate more suitable for real time imaging. To take advantage of these different strengths image fusion system have been developed which enable visualization of a patient's anatomy with both ultrasound and CT or both ultrasound and MRI. A common implementation is to view images from both modalities in co-registration, that is, overlaying (fusing) two images of the same anatomy together in a common display. So-called fusion imaging systems thereby take advantage of the strengths of both modalities. A CT or MRI image can be used for navigation, for instance, while the fused ultrasound image enables the movement of tissues and blood flow to be viewed in real time.

To create high quality ultrasound images it is necessary that there be good acoustic contact between an ultrasound probe and the body of the patient being scanned. Good acoustic contact is facilitated by the application of coupling gel to the probe and skin of the patient and by sonographers maintaining good acoustic coupling by forcefully pressing the ultrasound probe against the skin of the patient. When the probe is placed against soft tissue as is the case during abdominal scanning, for example, the force of the probe against the body will depress the skin and body where the probe is in contact with the patient. This is not the case with MRI or CT imaging, where the magnetic field or radiation beams pass through the air and readily penetrate the body without physical contact of an instrument. Consequently, the soft tissue and organs seen in CT and MRI images are uncompressed, whereas the same tissue and organs can be significantly compressed by the probe during ultrasound imaging of the same anatomy. As a result, the physical differences between the uncompressed anatomy in a CT or MRI image and the compressed anatomy in an ultrasound image can make the co-registration and fusing of the two images difficult. Accordingly it is desirable to be able to correct for this compression induced by the ultrasound probe so that the two images can be accurately fused into a single display of the anatomy under diagnosis.

Document US 2014/0193053 discloses a system and method for automatically fusing pre-operative images and intra-operative images. The pre-operative images (reference images) are transformed based on the intra-operative images.

SUMMARY OF THE INVENTION

Accordingly, it is an object of the present invention to provide a technique for recognizing and correcting for the soft tissue compression induced by ultrasound probe pressure when two images are to be co-registered and fused together.

It is a further object of the present invention to provide a simple and reliable technique for identifying probe pressure compression.

It is a further object of the present invention to modify reference CT or MRI images so that they can be more accurately co-registered with an ultrasound image.

The invention is defined by the claims.

In accordance with the principles of the present invention, a fusion imaging system is described in which real time ultrasound images are fused with reference images such as those produced by MRI or CT imaging. In an illustrated implementation, previously acquired CT or MRI or ultrasound images are acquired by the fusion imaging system for fusion with live ultrasound images. An ultrasound system is operated in conjunction with a tracking system such as an electromagnetic (EM) tracking system so that the ultrasound probe and images can be spatially tracked. A computerized image processor registers the probe position with a reference image of the anatomy being scanned by the probe and determines whether the probe appears to be inside the surface of the subject. For an external probe pressed against the exterior of the body the surface is the skin line. For an internal probe the surface is generally the outer surface of the organ being scanned. If the probe appears to be inside the surface, it is due to probe compression of the subject, and the reference image is modified to locate the skin line or organ surface in the reference image in front of the ultrasound probe. The modified reference image can then be readily co-registered and fused with an ultrasound image produced by the probe.

DETAILED DESCRIPTION OF THE EMBODIMENTS

Figure 1:
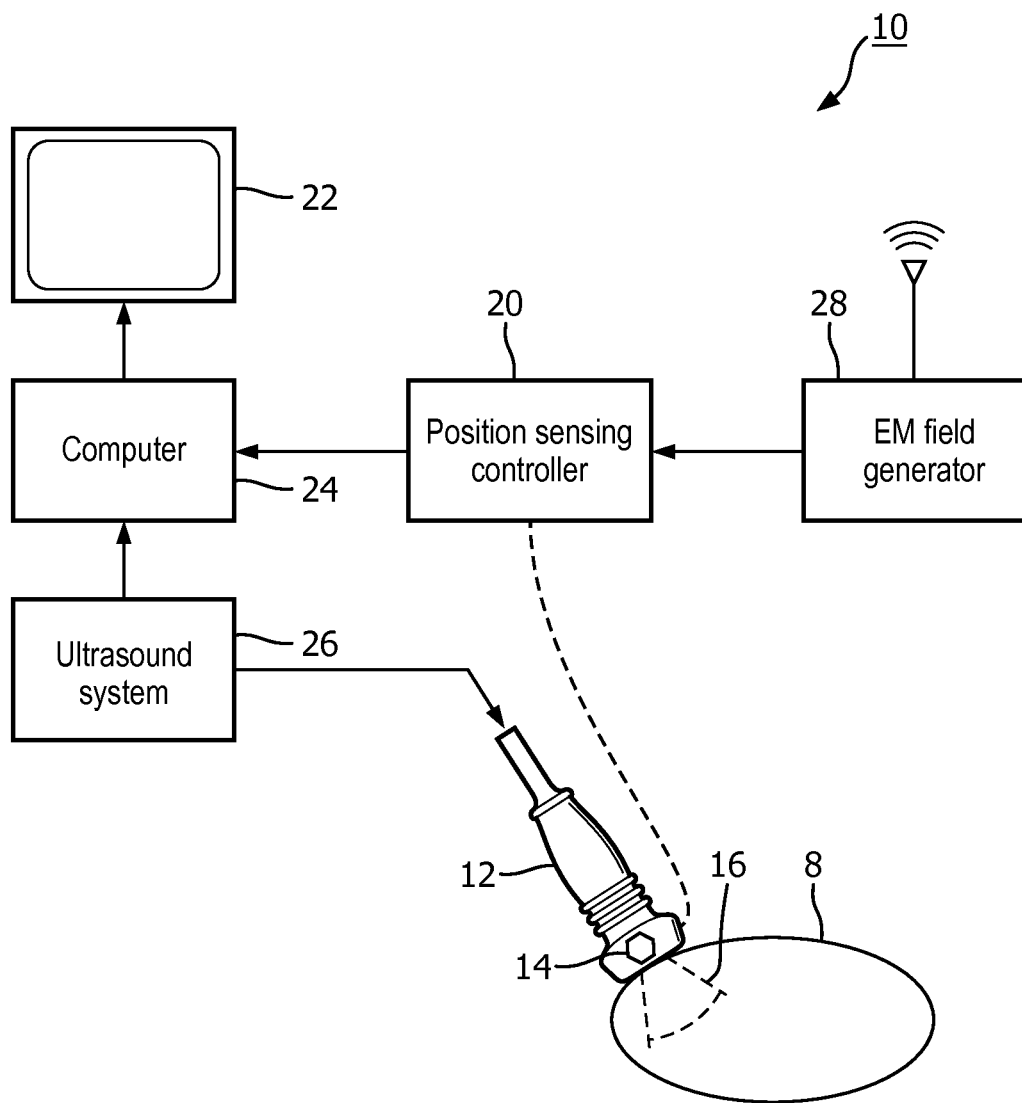
FIG. 1 illustrates an image fusion system operating with an EM tracking system and an ultrasound imaging system.

Referring first to FIG. 1, an image fusion system operating with an EM tracking system and an ultrasound imaging system is shown in block diagram form. A system such as that shown in FIG. 1 is commercially available from Philips Healthcare of Andover, Mass. as the Epiq™ ultrasound system with the Percunav EM tracking feature. An ultrasound imaging system 26 has a probe 12 which is pressed against the skin of a subject 8 to ultrasonically image internal tissue and organs of the subject. The EM tracking feature includes a computer 24 which receives reference images such as previously obtained CT or MRI images of the subject and fuses real time ultrasound images from the ultrasound system 26 with reference images. The computer 24 is a general digital computer or processor, a control processor, a digital signal processor, an application specific integrated circuit, a field programmable gate array, a digital circuit, an analog circuit, or combinations thereof or other now known or later developed device which is capable of or can be programmed to register ultrasonic image data with diagnostic images. The EM tracking feature also includes an EM field generator 28 and a position sensing controller 20. The EM field generator 28 radiates a variable electromagnetic field which permeates the subject 8 and the space in which the ultrasonic scanning is performed. Attached to the probe is a probe orientation sensor 14 which detects the electromagnetic field and relays information about the field either by wire or wirelessly as indicated by the dashed line to a position sensing controller 20. The position sensing controller processes this information to compute the position and orientation of the ultrasound probe 12. This data identifies the position and orientation of the probe aperture at the tip of the probe and also the position and orientation of the image plane or volume which is being instantaneously scanned by the probe, such as image plane 16 inside the subject in front of the probe. The position sensing controller reports this information to the computer 24, which uses it to track and orient images of the image plane or volume 16 produced by the probe and ultrasound system in relation to reference images. The computer does this by first co-registering an ultrasound image to a reference image as described below. Thereafter as the probe is moved during scanning of the subject, its instantaneous position and orientation is continuously reported to the computer by the position sensing controller and the computer is able to use this tracking information to continuously maintain registration of the ultrasound images with the previously acquired reference images. The fused ultrasound and reference images are displayed on image display 22. Further details of a system such as shown in FIG. 1 may be found in the Epiq Percunav user manual distributed with the Epiq ultrasound system, in U.S. Pat. No. 6,216,029 (Paltieli), and in U.S. Pat. No. 4,945,305 (Blood) for example.

Suppose that the system of FIG. 1 is being used to diagnose the liver of a subject. The liver is thus the region of interest in this example. Further suppose that the torso of the subject including the liver has previously been scanned by CT imaging as illustrated in FIG. 2, and that these CT images have been loaded into the computer of FIG. 1 to be used as reference images during live ultrasound scanning. As the live ultrasound images of the region of interest are produced the system is first calibrated, and thereafter the live ultrasound images are co-registered to images of the CT scan. Calibration of the ultrasound and EM tracking system can be done in various ways. One way is for the clinician to scan the patient to produce images showing anatomical landmarks such as the hepatic duct or the falciform ligament of the liver. These anatomical landmarks can be co-registered with the same landmarks in the reference images, as by clicking on them in the reference and ultrasound images with a pointing device such as a mouse or trackball. The computer will then co-register the ultrasound and reference images when guided by this user input. Image processing can also be used to orient and align an ultrasound image with a reference image. The Epiq Percunav feature provides another calibration technique, which is to place a fiducial device on the patient. The fiducial device is immediately identified by the EM tracking system. The clinician then places the ultrasound probe in contact with the fiducial device and the computer then co-registers the ultrasound probe and the fiducial device to a common inertial system such as that of the EM field radiated by the EM field generator.

Once the EM tracking system has been calibrated the clinician begins scanning the patient and the computer 24 will align the real time ultrasound images with the corresponding planes or volumes of the reference image dataset. In this example the clinician is examining the liver, and so the registration software program executed by the computer is trying to segment exactly the same region of interest, a liver, out of at least two different images. The segmentation program in this example begins by deforming an initial model such as a shape model that roughly represents the shape of the target object. In the example of the target object being a liver, the initial shape might be a sphere or a liver mean shape. This shape is represented by an implicit function, i.e., a function $\Phi$, defined in the whole space, which is positive inside the shape and negative outside. The shape is then the zero level-set of such a function. The whole implicit function is deformed by a space transformation $\psi$. In particular, the zero level-set will change and so will the corresponding object. This transformation is decomposed into two transformations of different kinds that will correct the initial pose of the model:

$$\psi = \xi \cdot G;$$

where G is a global transformation that can translate, rotate or rescale the initial shape and $\xi$ is a local deformation that will actually deform the object so that it matches more precisely the object to segment in the image.

The goal of the method is then to find the best $\xi$ and G, using the image I information. This is done by minimizing the following energy:

$$\int H(\Phi \cdot \xi \cdot G(x)) r(x) + \lambda \int \|\xi(x) - x\|^2$$

In the first term, also called data fidelity, H is the Heaviside function (H(x)=1 if x>0 and 0 if x<0) which means that the integral is actually only inside the deformed object. r(x) is an image-based function that returns at each point a negative (or positive) value if the voxel is likely to be outside (or inside) the object of interest. For ambiguous regions, r(x) is set to zero. The second term is the so-called regularization. The second term is the norm between $\xi$ and the identity function. The amplitude of the deformation is constrained because the object shape should not deviate too much from the prior shape. It is to be emphasized that this second term is independent from the position and orientation of the object which was the purpose of the decomposition of the transformation. The minimization of such energy is performed using a gradient descent on both $\xi$ and G at the same time.

In a simple example of only two images, and if the two images were already perfectly registered, then the previously described equation can easily be extended by adding another data fidelity term:

$$\int H(\Phi \cdot \xi \cdot G(x)) r1(x) + \int H(\Phi \cdot \xi \cdot G(x)) r2(x) + \lambda \int \|\xi(x) - x\|^2$$

However, a registered acquisition might only take place if both images were acquired simultaneously or shortly after one another. It is very unlikely that the images would be registered if acquired subsequently. Hence, this possibility is taken into account with another transformation. In general, this further transformation might be non-rigid and of any type. However, if an assumption of looking for the same object can be made, this transformation (denoted G12) can be rigid, i.e., it allows a global change of position and orientation but only with the same size target. The transformation G12 could also be set to any affine transform to take into account volume changes, without loss of computational efficiency. The energy then becomes:

$$\int H(\Phi \cdot \xi \cdot G(x)) r1(x) + \int H(\Phi \cdot \xi \cdot G(x)) r2(x) \cdot G12(x) + \lambda \int \|\xi(x) - x\|^2$$

Basically, this equation corrects the image information coming from the second term by the transformation G12. In case of the registration of more than two images, further terms for each image, each comprising its own transformation, would be added.

The third term, which is optional, is constructed as a constraint to the local deformation. It restrains the deformation if the local deformation causes the shape of the object to deviate too much from the initial geometric shape. Hence, as we search for a minimum, in case the first and the second term lead to the same results, the solution transforming the initial geometric shape less than the other solutions will be considered best. The parameter "λ" may be set to determine the relevance of this constraint.

The optimization is performed by gradient descent simultaneously on ξ, G, and G12. At the end, a segmentation as the zero level-set of the function Φ·ξ·G is more precise because it uses the information of the two images. Further, estimation of the transformation G12 allows registration of the images to each other to be more precisely achieved.

Figures 2A, 2B:
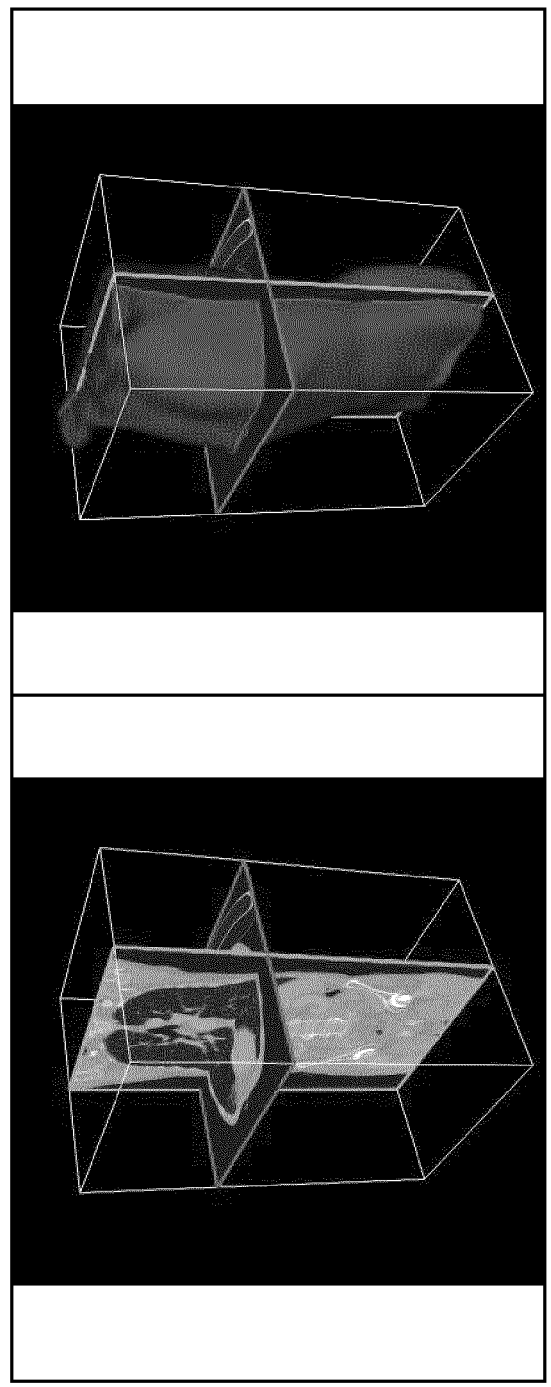
FIG. 2 illustrates a tomographic CT image of the torso of a subject and a surface rendering showing the skin of the torso.

A preferred implementation of the present invention utilizes a system such as that illustrated in FIG. 1, and makes use of the fact that reference images such as those produced by CT or MRI scanning of a patient can image not only the internal anatomy of a subject but the whole body of a subject out to and including the subject's skin surface. For instance, FIG. 2a illustrates two tomographic images of a subject produced by CT scanning. In the 3D reference grid shown are an image of a longitudinal plane of the subject and also a transverse image of the internal anatomy of the subject. FIG. 2b illustrates, in the same 3D grid system, a surface rendering of the exterior of the torso of the same subject, illustrating that the CT imaging captures the full body of the subject including the skin line. A preferred implementation of the present invention utilizes this capture of the patient's skin line in the reference images to determine whether modification of the reference images is necessary in order to better co-register the reference and ultrasound images.

Figure 3:
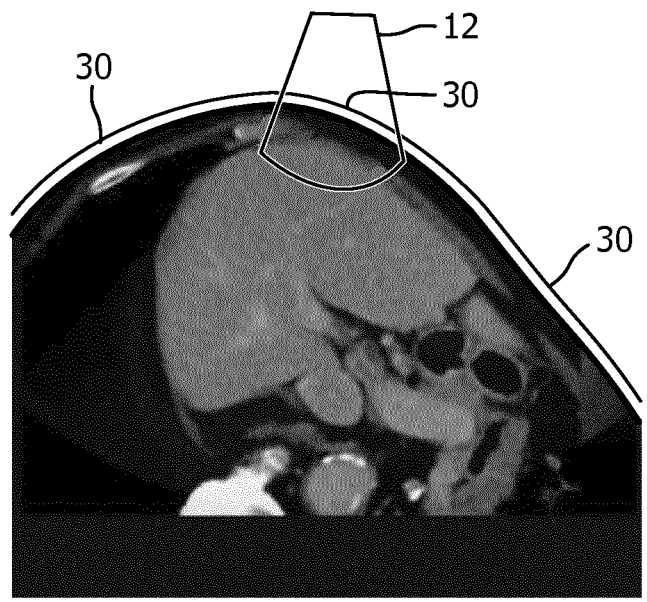
FIG. 3 illustrates a reference CT image in spatial registration with an ultrasound probe represented by a probe icon.

How this is accomplished is illustrated by the CT reference image of FIG. 3, which extends out to the skin surface 30. Overlaying the reference image, and in the same spatial coordinate system through use of EM tracking, is an icon 12 representing the location of the ultrasound probe 12. The computer 24 can locate the icon 12 as a graphic overlay using the position and orientation coordinates of the probe as reported by the position sensing controller, positioning the icon in relation to the reference image coordinates spatially related to the ultrasound image by the co-registration process described above. A simpler approach is to locate the icon at the top of the co-registered ultrasound image, since the ultrasound image emanates from the face (lens) of the probe. For a sector image this is simply locating the icon at the apex of the image sector. It appears from the image in FIG. 3 that the external ultrasound probe (icon 12) has actually penetrated into the body of the subject in the reference image. The reason for this appearance is that the clinician performing the ultrasound scan is pressing firmly against the abdomen in order to acquire artifact-free ultrasound images, compressing the abdomen inward with the probe. Hence, when the probe position 12 and the reference image are spatially registered, the probe position during deformation of the abdomen appears to be inside the body of the patient in the reference image, where no compression was applied.

In particular, the probe 12 appears to be inside the skin surface 30 of the patient. An implementation of the present invention identifies the skin 30 by segmenting it in the reference image. This segmentation process is both simple and reliable because the skin 30 is the outer surface of the subject in the CT or MRI image. The side of the skin surface occupied by tissue and organs in the image is the inside of the body of the subject and the other side, where the subject's clothing and air return no signal, is the outside of the body. Thus, when the location of the probe 12 is found to be inside the body in the reference image, the system concludes that this is due compression of the body by the probe during ultrasound scanning.

Figure 4:
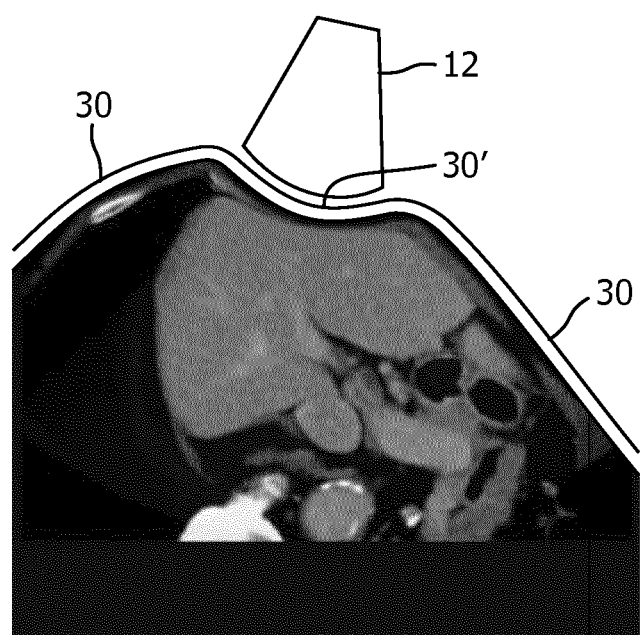
FIG. 4 illustrates a reference image in a fusion imaging system which has been corrected for probe compression in accordance with the principles of the present invention.

The correction of the anomaly is then straightforward. The reference image is deformed so that it will more readily register with the ultrasound image, in which the outer tissue is compressed due to probe pressure. This is done by the computer redrawing the skin surface so that the surface 30' does not overlap with and is in front of the probe as shown in FIG. 4. The skin surface can be smoothly redrawn by computer by spline fitting and/or affine transform algorithms, for instance. Several approaches can be taken to modify the tissue and organs in front of the probe in the reference image. The easiest approach is simply to truncate the tissue and organ structure that overlaps the probe so that all of the tissue in the image is inside the redrawn skin surface 30' as shown in FIG. 4. In a case where the reference image is to play a role in the diagnosis or more precision is desired, a more sophisticated approach can be taken. That is to recast the tissue and organ structure in front of the probe with an appearance of greater density and/or stiffness than in the original reference image, in recognition of the fact that it is being compressed by the probe. Tissue and organs closest to the probe can be recast with the greatest density and/or stiffness, with the new characteristic declining over a certain distance into the body. A distance over which this appearance of a declining density and/or stiffness gradient is created can be established for different organs and parts of the body in consideration of the nominal density and/or stiffness of particular parts of the body. For the liver, the predetermined distance of the declining gradient could be 2 cm, whereas for the prostrate the gradient distance might only be 0.25 cm. For cases where the reference image is only to be used for navigation and the ultrasound image will be the basis for the diagnosis, simple truncation of the tissue and organs appearing outside the redrawn skin surface will generally suffice.

Figure 5:
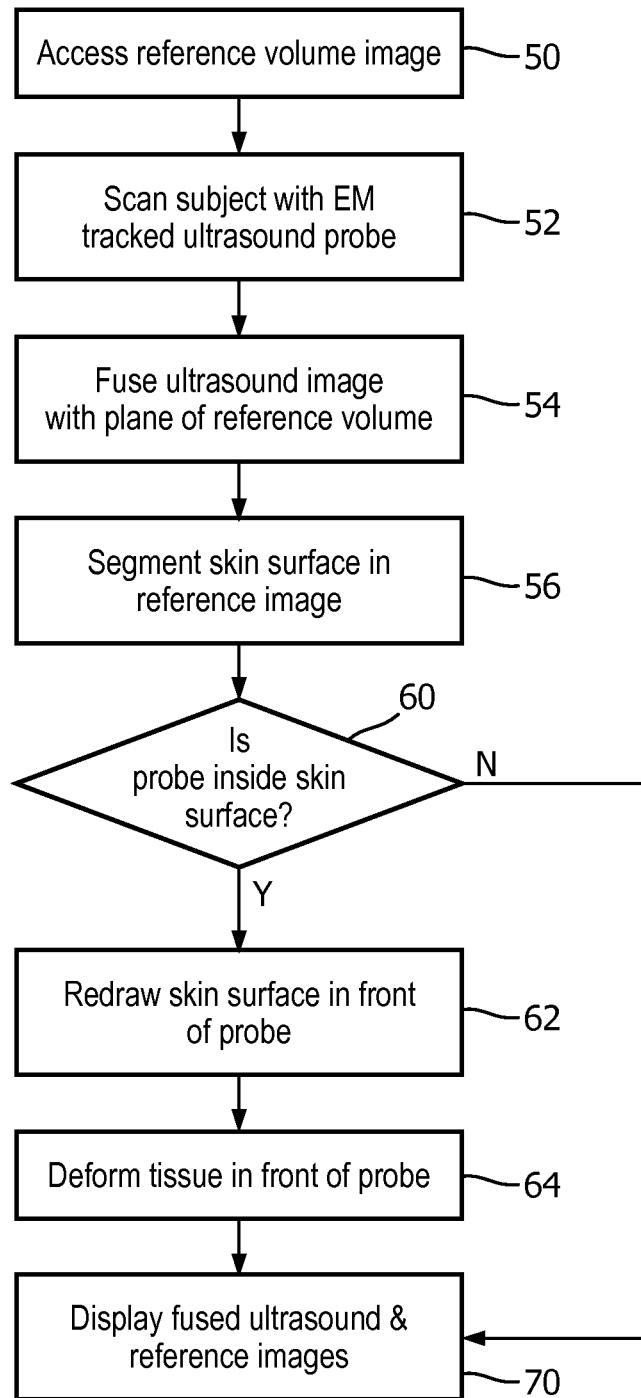
FIG. 5 is a flowchart of a preferred method for correcting for ultrasound probe compression in an image fusion system.

FIG. 5 is a flowchart illustrating a preferred process for implementing the present invention with the system of FIG. 1. At step 50 the computer 24 accesses 2D or 3D reference images. This may be in the form of a 3D volume dataset from which either 2D images or 3D volume images may be extracted by multiplanar reconstruction, for instance. In some implementations the computer 24 may be part of a PACS system with reference CT or MRI data delivered to the computer over a hospital data network. In other implementations the computer 24 may be a modularized processor of the ultrasound system as it is in the Epiq ultrasound system. At 52 a subject is ultrasonically imaged with an EM tracked ultrasound probe 12. At 54, in the case of 2D imaging, the computer fuses (co-registers) an ultrasound image with a plane of the reference image data. In the case of 3D imaging, an ultrasonic volume image would be fused with a reference volume image. It will be appreciated from FIG. 3 that an implementation of the present invention need not fuse an entire ultrasound image with a reference image when the spatial coordinates of the probe and the reference image are both known in the same inertial reference system. In that case, it is sufficient to co-register just a probe icon with a reference image as shown in FIG. 3. In step 56 the computer program segments the skin surface 30 in the reference image, and in step 60 the computer program determines whether the location of the probe 12 appears to be inside the skin surface, e.g., as shown in FIG. 3. If not, the fused ultrasound and reference images are displayed on the image display 22 as indicated by step 70. If the answer to the inquiry is yes, the skin surface in the reference image is redrawn in step 62 as shown at 30' in FIG. 4 and explained above. The tissue in front of the probe is deformed in step 64 so that it is contained within the redrawn skin surface 30'. With these modifications the probe location will now appear to be outside the skin 30' as shown in FIG. 4. The modified reference image may now be readily fused with the ultrasound image in which the skin and body is depressed by probe pressure, and displayed on the image display 22.

The concepts of the present invention can address the same problem caused by an internal probe such as an intracavity probe used to image the prostate. In that case, probe pressure can compress and distend the prostate in the ultrasound image compared to a CT image of the prostate in which no pressure is exerted against the organ. The surface of the probe in the CT image can be modified as described above so that both the CT and ultrasound images of the organ are in good registration.

The invention claimed is:

1. A medical image fusion system comprising:
   a computer capable of processing medical images;
   a source of previously acquired reference images, the images comprising a region of interest in a body having a surface;
   an ultrasound system comprising a probe and configured to acquire ultrasound images;
   a spatial tracking system, coupled to the probe, and arranged to track the spatial location of the probe during image acquisition;
   wherein the computer is adapted to align the ultrasound images acquired by the ultrasound probe and the reference images, based, at least in part, on minimizing an energy value calculated from a global transformation and a local deformation,
   wherein the computer is further adapted to determine from the tracked probe location whether the probe location is at least partially inside the surface of the body shown in a spatially corresponding reference image, and, if so,
   wherein the computer is further adapted to modify the reference image, wherein the modifying of the reference image comprises:
      displaying the probe location outside the surface of the body shown in the reference image;
      redrawing the surface shown in the reference image;
      deforming tissue in front of the probe location and inside the redrawn surface in the reference image based, at least in part, on the global transformation and the local deformation; and
      recasting an appearance of the tissue deformed in the reference image contained within the redrawn surface based on an increase in the density and/or stiffness of the tissue due to compression of the tissue by the probe.

2. The medical image fusion system of claim 1, wherein the reference images further comprise CT or MRI images.

3. The medical image fusion system of claim 2, wherein the CT or MRI images further comprise a 3D image dataset.

4. The medical image fusion system of claim 1, wherein the spatial tracking system further comprises an EM tracking system.

5. The medical image fusion system of claim 4, wherein the EM tracking system further comprises:
   an EM field generator;
   a probe orientation sensor attached to the probe; and
   a position sensing controller.

6. The medical image fusion system of claim 5, wherein the position sensing controller further produces position and orientation information about the probe,
   wherein the position and orientation information is provided to the computer.

7. The medical image fusion system of claim 1, wherein the computer is further adapted to fuse a modified reference image with an ultrasound image.

8. The medical image fusion system of claim 1, wherein the computer is further adapted to fuse modified reference images with ultrasound images in real time.

9. The medical image fusion system of claim 1, wherein an estimation of the energy value comprises a data fidelity term and a regularization term.

10. The medical image fusion system of claim 9, wherein the data fidelity term comprises a Heaviside function.

11. The medical image fusion system of claim 1, wherein the surface of the reference image is redrawn by a spline fitting algorithm.

12. The medical image fusion system of claim 1, wherein the surface of the reference image is redrawn by an affine transform algorithm.

* * * * *